United States Patent [19]
Faix et al.

[11] Patent Number: 4,743,339
[45] Date of Patent: May 10, 1988

[54] METHOD FOR CONTROLLING THE DIGESTION OF PULP BY IR SPECTROSCOPY

[76] Inventors: Oskar Faix, Schützenstrasse 40, 2057 Reinbek; Ulrich Welkener, Weddestrasse 92, 2000 Hamburg 74; Rudolf Patt, Lohbrügger Str. 3a, 2057 Reinbek, all of Fed. Rep. of Germany

[21] Appl. No.: 889,222

[22] Filed: Jul. 25, 1986

[30] Foreign Application Priority Data

May 13, 1986 [DE] Fed. Rep. of Germany ....... 3616051

[51] Int. Cl.$^4$ .............................................. D21C 7/12
[52] U.S. Cl. ........................................ 162/49; 162/61
[58] Field of Search ..................... 162/238, 49, 62, 61, 162/263, 198, DIG. 10

[56] References Cited

U.S. PATENT DOCUMENTS 4,540,468  9/1985  Genco et al. ........................ 162/49

OTHER PUBLICATIONS

Tikka et al., "A New Kraft Pulping Analyzer for Monitoring Organic and Organic Substances", *Tappi Journal*, Jun. 1986; published 1985 Pulping Conf. Proceedings.
*Perry's Chemical Engineering Handbook*, 4th Ed., Perry et al., ed.; New York, 1963, Chapt. 2-75.

*Primary Examiner*—Steve Alvo
*Attorney, Agent, or Firm*—Dressler, Goldsmith, Shore, Sutker & Milnamow, Ltd.

[57] ABSTRACT

A method is described for controlling the cooking degree of pulp during pulp digestion and for analyzing cooking chemical composition and -concentration before and during cooking operation. The method is based on the continuous or discontinuous monitoring of the IR spectroscopical behavior of the cooking liquor. Evaluated IR-spectal data of cooking liquor samples are correlated with analytical data of the cooking liquor on the one hand and the resulting pulp on the other hand by means of adequate mathematical/statistical methods. A feedback of analytical data is performed to improve the statistical relevance of the method. The invention provides a method for cooking control which is much more accurate and faster than existing control methods.

10 Claims, 11 Drawing Sheets

INDUSTRIAL BISULFITE COOK

FIG 1a: LABORATORY BISULFITE COOK

FIG 1b: INDUSTRIAL BISULFITE COOK

FIG. 2a   LABORATORY BISULFATE COOK

FIG. 2b: INDUSTRIAL BISULFITE COOK

FIG. 3: LABORATORY SULFATE COOK

FIG 4a: COOKING CHEMICAL COMPOSITION OF A SODIUM BISULFITE COOK

FIG. 5: CORRELATION BETWEEN INTEGRATED BAND AREAS AND KAPPA NUMBERS OF THE PULPS.

FIG. 6 CORRELATION BETWEEN BAND INTENSITIES AND KAPPA NUMBERS OF THE PULPS

FIG. 7: CORRELATION BETWEEN INTEGRATED BAND AREAS AND KAPPA NUMBERS OF THE PULPS

FIG. 8 CORRELATION BETWEEN BAND INTENSITIES AND KAPPA NUMBERS OF THE PULPS

METHOD FOR CONTROLLING THE DIGESTION OF PULP BY IR SPECTROSCOPY

BACKGROUND OF THE INVENTION

The invention relates to a method for controlling the cooking degree of lignocelluloses as well as the pulp digesting operation by means of a FTIR (Fourier transform infrared) spectrometer for monitoring the infrared absorption of cooking liquors.

Continuous direct measurement of lignin concentration in cooking liquors during digesting operation has not been possible so far. Parameters influencing the digestion of lignocelluloses are therefore commonly used for cooking control in pulp mill process control systems. These parameters are cooking temperature, duration of the cook, digester pressure as well as concentration and composition of the cooking liquor. Even in combined so-called feedback/ feed forward systems (Bylund, L.; Hägglund, S.; Thorsell, L.; Wallin, G.: On-line cooking liquor analyzer - A means for effective control of sulfite digesters. 1982 International Sulfite Pulping Conference, Toronto, Oct. 20-22, 1982, TAPPI Proceedings 285-292) the cooking degree can only indirectly be determined, and the resulting kappa number deviations of the pulps from a preset value are relatively high. Kappa number is a measure of the residual lignin content of the pulp.

For that reason investigations have been made for some time to examine the applicability of fluorescence spectroscopy (Bublitz, W. J.: Fluorescence of pulping liquors: A tool for digester control? TAPPI 64 (6), 73-76 (1981)) as well as light- and ultraviolet-photometry (Helmke, D.: Untersuchungen über die Eignung der UV-Absorptionsmessung von Bisulfitablaugen zur Aufschlusskontrolle bei Zellstoffkochungen. Dissertation, Universität Hamburg, 1973 and Tikka, P.O.; Virkola, N.-E.: A new cooking analyzer for monitoring organic and inorganic substances. 1984 Pulping Conference, San Francisco, Nov. 12-14, 1984, TAPPI Proceedings 291-296) for the determination of lignin concentration in cooking liquors. It became evident that either no good correlation existed between kappa number of the pulps and the measured lignin concentration in the liquor at the end of the cooks or that the time spent on the exact measurement of lignin concentration in the cooking liquor was quite long.

The present invention provides a method which overcomes these disadvantages.

SUMMARY OF THE INVENTION

The present invention provides a method for directly and continuously analyzing cooking liquors of all pulping processes during the digestion period with regard to delignification and cooking chemical composition and -concentration.

Samples of cooking liquors taken during the cooking cycle are analyzed by Fourier transform infrared (FTIR) spectroscopy. The absorbance of a sample is measured and an IR-data set is derived from the spectrum. This IR-data set has a close relationship with analytical data of the cooking liquor. This relationship has to be established within a predetermined period. During this period IR-data sets are correlated to analytical data of the cooking liquor and to analytical data of the resulting pulps, e.g. the remaining lignin content determined e.g. as kappa number according to TAPPI Standard T 236, by means of regression analyses or other adequate mathematical/statistical methods.

The present invention provides a method for rapid and accurate determination of cooking chemical concentration and composition as well as concentration of organic substances in the cooking liquor. Contrary to other methods it is not necessary to dilute, to fractionate or to modify the cooking liquors prior to IR absorption measurements. In addition no influence of cooking temperature, digester pressure, and chemical concentration of the liquor could be detected over the lignin concentration measurement by IR absorption.

The infrared absorption in the mid- or near-IR region can be measured by transmission or by attenuated total reflectance (ATR). In both cases samples can be taken manually or automatically by means of a connecting pipe between digester and flow-through cuvette. After the absorbance measurement a specific IR-data set - specific for each pulping process and wood species - is established by mathematical evaluation of the spectra. That is done by measuring base-line corrected band intensities and/or -areas and/or absorbance curves of each spectrum or parts thereof. After a sufficient number of cooks IR-data sets and analytical data sets are combined by means of simple linear—or multiple regression analysis or by least square curve fitting. Continual analytical control of cooking liquors and pulps with subsequent input of the determined data into the correlation equations improves the statistical relevance.

A FTIR spectrometer with a modified software with regard to mathematical/statistical data handling provides reliable data for determining the end of the pulp cooking procedure.

But it might as well be integrated into existing process control systems. The determined data are fed manually or on-line to a computational unit of the process control system where they are used for optimizing the cooking operation, e.g. to give the operator information when to stop the delignification process.

The invention is illustrated in the accompanying drawings in which:

FIGS. 1 and 2 are referred to in Example 1.

The following examples illustrate the scope and nature of the present invention. All infrared measurements were performed on a Nicolet 20 SX FTIR spectrometer under the following conditions:
Cell windows : Irtran 2 ( ZnS )
Cell thickness: 0.025 mm
Number of scans : 200
Spectral resolution : 1 cm$^{-1}$
All samples were cooled and the transmittance measured at room temperature.

EXAMPLE 1

The progress of a magnesium bisulfite cook of beech chips is demonstrated by increase of the lignin concentration in the cooking liquor during the cook for
(a) a laboratory cook and
(b) an industrial cook.

Figure 1A:
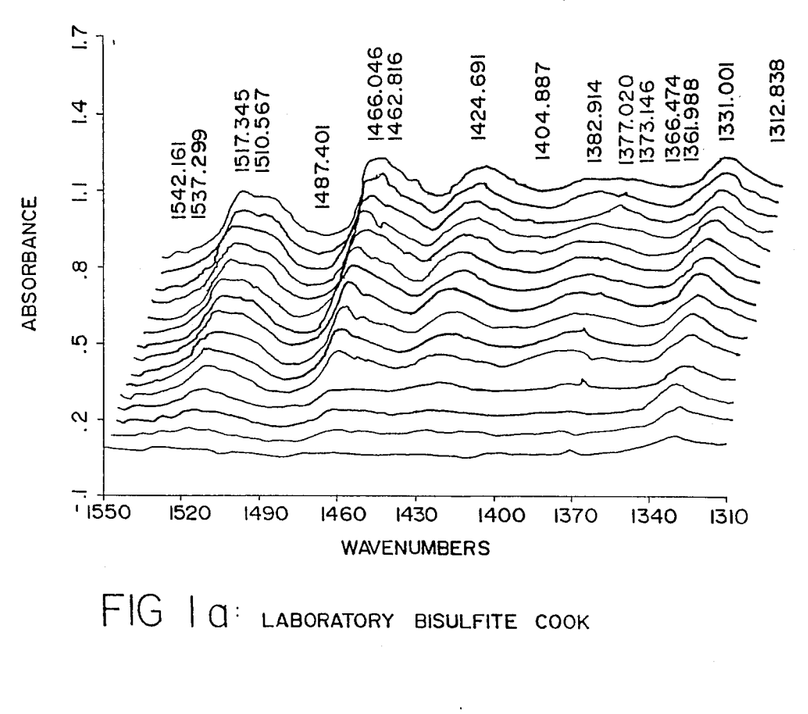
FIG. 1a is a perspective view showing a progression of curves taken at progressing times in which absorbance is plotted against wavenumbers to detail the progress of a laboroatory bisulfite cook.
Figure 1B:
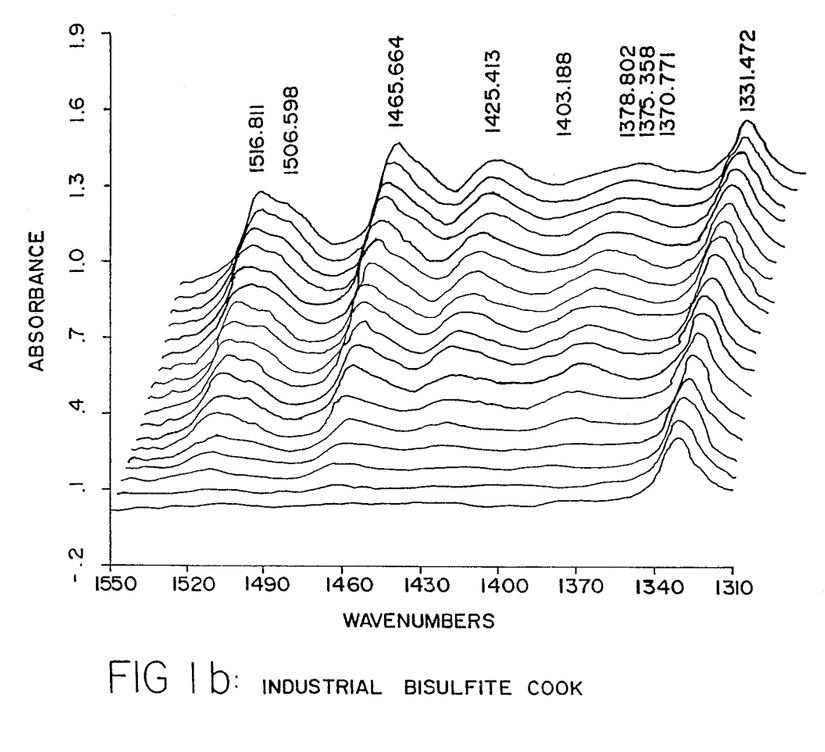
FIG. 1b is the same as FIG. 1a except that the progress of an industrial bisulfite cook is shown.

In FIG. 1a and 1b the increase of absorbances can be seen of two bands having maxima at ca. 1515 cm$^{-1}$ and 1465 cm$^{-1}$, respectively.

Figure 2A:
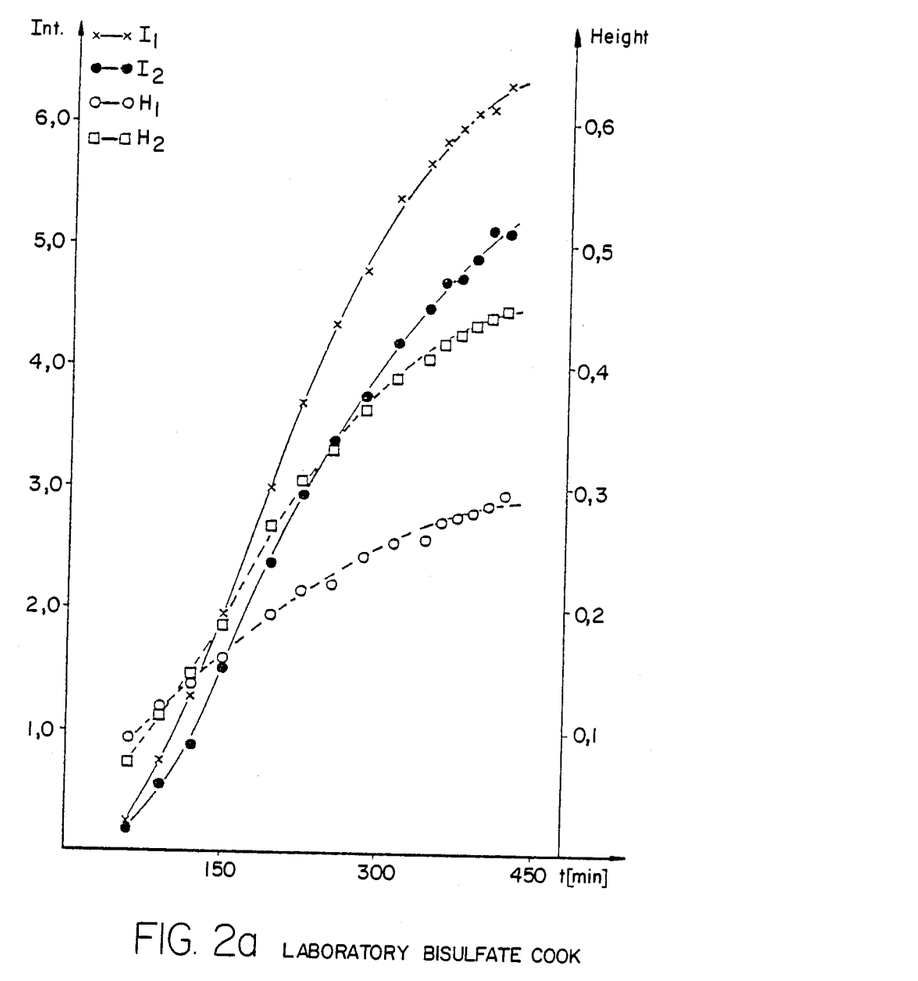
FIG. 2a is a graph in which four integrated band areas are plotted against progressing time for a laboratory bisulfite cook using the data plotted in FIG. 1a, and FIG. 2a shows the same thing using the data plotted in FIG. 1b. These
Figure 2B:
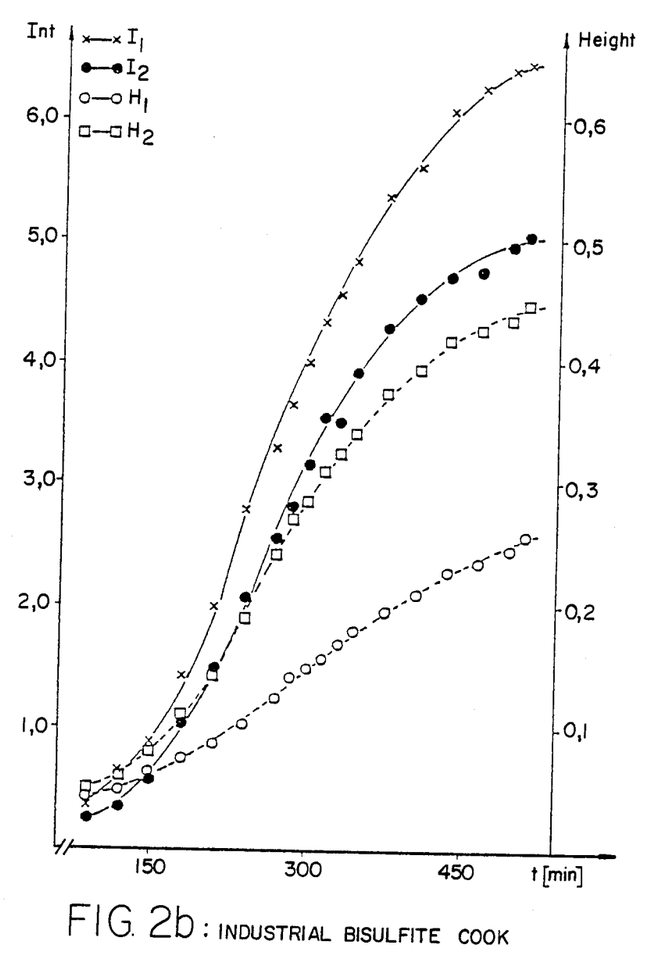

In FIG. 2a and 2b plots show the increase of integrated band areas ($I_1, I_2$) and band heights ($H_1, H_2$) vs. cooking time for the same two bands. Cooking conditions for
(a) the laboratory cook:
Cooking liquor concentration: 6.65% total $SO_2$, 3.38% free
  $SO_2$, 2.13% MgO
Amount of chips: 800 g oven dried (o.d.) weight
Mini-mill digester: M/K Systems Inc.
Liquor/wood ratio: 3.5:1
Heating up period: 65 min
Time at maximum temperature ($T_{max}$): 360 min
$T_{max}$: 140° C.
Digester pressure (p) at $T_{max}$: 6.3 bar
Kappa number of the resulting pulp: 22.3.
(b) the industrial cook:
Cooking liquor concentration: 5.50 % total $SO_2$, 1.08 % free $SO_2$, 1.38 % MgO
Amount of chips : 64 t o.d. weight
Digester: 225 m$^3$ stainless steel
Liquor/wood ratio: 2.5:1
Heating up period: 195 min
Time at $T_{max}$: 265 min
$T_{max}$: 139° C.
p at $T_{max}$: 5.5 bar
Kappa number of the resulting pulp: 17.2.

EXAMPLE 2

Figure 3:
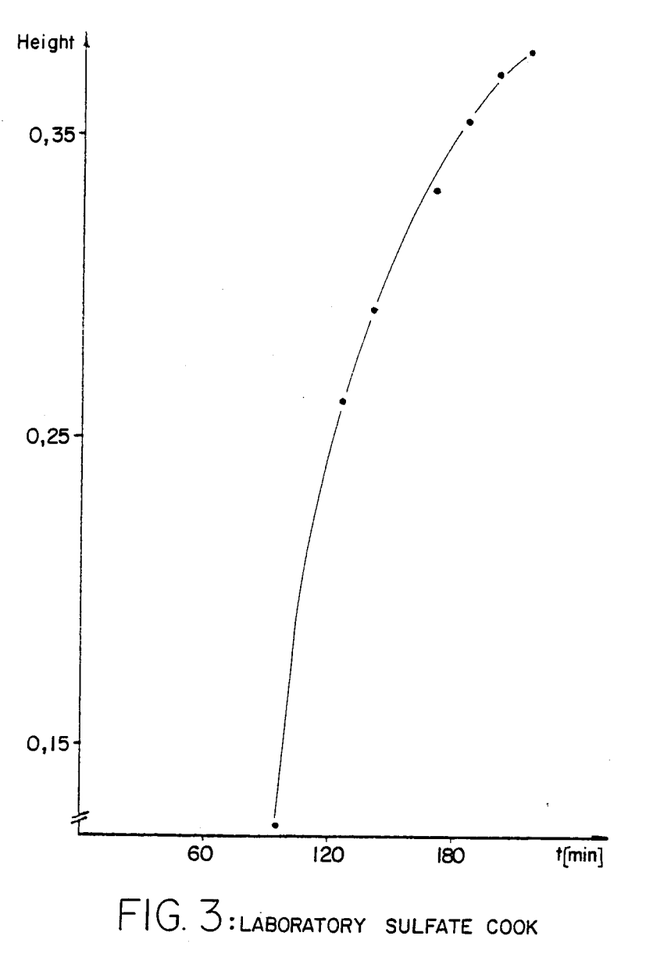
FIG. 3 shows the increasing band absorbance intensities at about 1494 $cm_{-1}$ vs. cooking time with respect to the laboratory sulfate cook described in Example 2.

The progress of a laboratory sulfate cook of spruce chips is evident from the plot of increasing band absorbance intensities at ca. 1494 cm$^{-1}$ vs. cooking time in FIG. 3.
Cooking conditions:
Chemicals: 19% NaOH/o.d. wood, 8% Na$_2$CO$_3$/o.d. wood, 10% Na$_2$S/o.d. wood
Amount of chips: 800 g o.d. weight
Mini-mill digester: M/K Systems Inc.
Liquor/wood ratio: 4:1
Heating up period: 95 min
Time at $T_{max}$: 120 min
$T_{max}$: 170° C.
p at $T_{max}$: 7.7 bar
Kappa number of the resulting pulp: 23.5

EXAMPLE 3

Figure 4A:
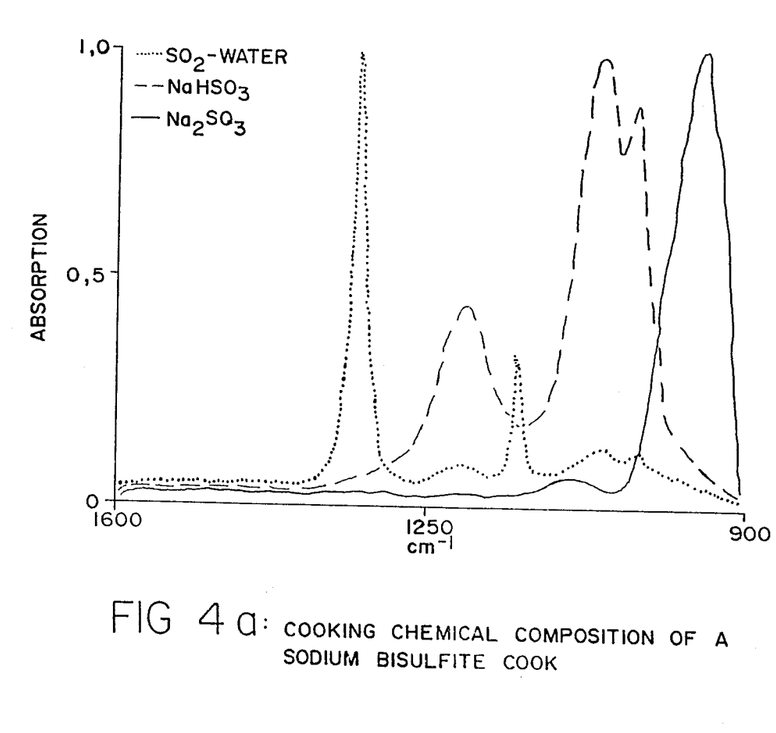
FIG. 4a is a graph comparing absorption vs reciprocal centimeters for an IR spectra to show the composition and concentration of chemicals in an acid sodium bisulfite cooking liquor as described in Example 3.
Figure 4B:
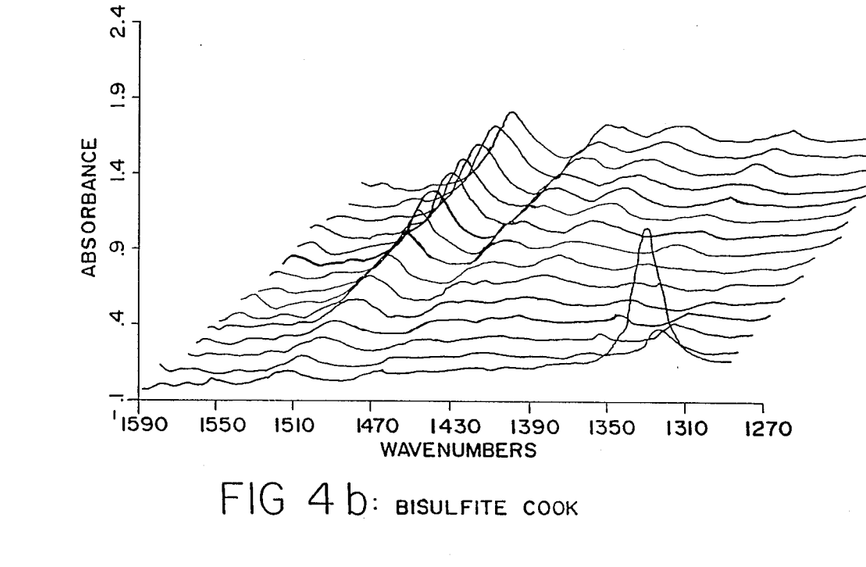
FIG. 4b shows the change of chemical composition during a sulfite cook of spruce chips.

The chemical composition and -concentration of an acid sodium bisulfite cooking liquor is determined by multicomponent analysis, e.g. the ratios of characteristic band intensities. FIG. 4a gives IR spectra of chemicals relevant for an acid sodium bisulfite cook with characteristic bands at ca. 960 cm$^{-1}$ for sodium sulfite, ca. 1215 cm$^{-1}$ for sodium bisulfite and ca. 1330 cm$^{-1}$ for $SO_2$-water ("free $SO_2$"). The change of relative chemical composition and -concentration during a sulfite cook of spruce chips is illustrated in FIG. 4b on the basis of the decrease of "free $SO_2$", i.e. the decrease of the band intensity at ca. 1330 cm$^{-1}$.
Cooking conditions:
Cooking liquor concentration: 7.82% total $SO_2$, 5.10% free $SO_2$, 0.86% MgO
Amount of chips: 58.2 t o.d. weight
Digester: 320 m$^3$ brick-lined steel
Liquor/wood ratio: 3.4:1
Heating up period: 180 min
Time at $T_{max}$: 270 min
$T_{max}$: 138° C.
p at $T_{max}$: 6.6 bar
Kappa number of the resulting pulp: 7.2

EXAMPLE 4

Figure 5:
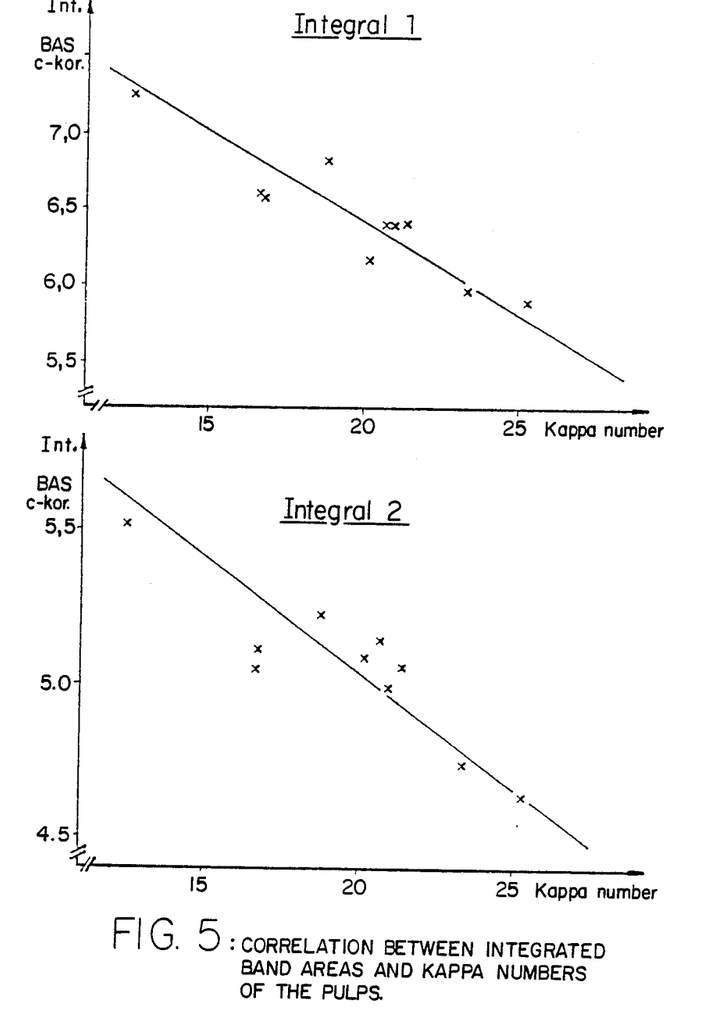
FIGS. 5 and 6 each show a pair of graphs referred to in Example 4 for a series of cooks of beech chips as set forth in Example 1 in which the integrated band areas are correlated with the kappa numbers of the pulps.
Figure 6:
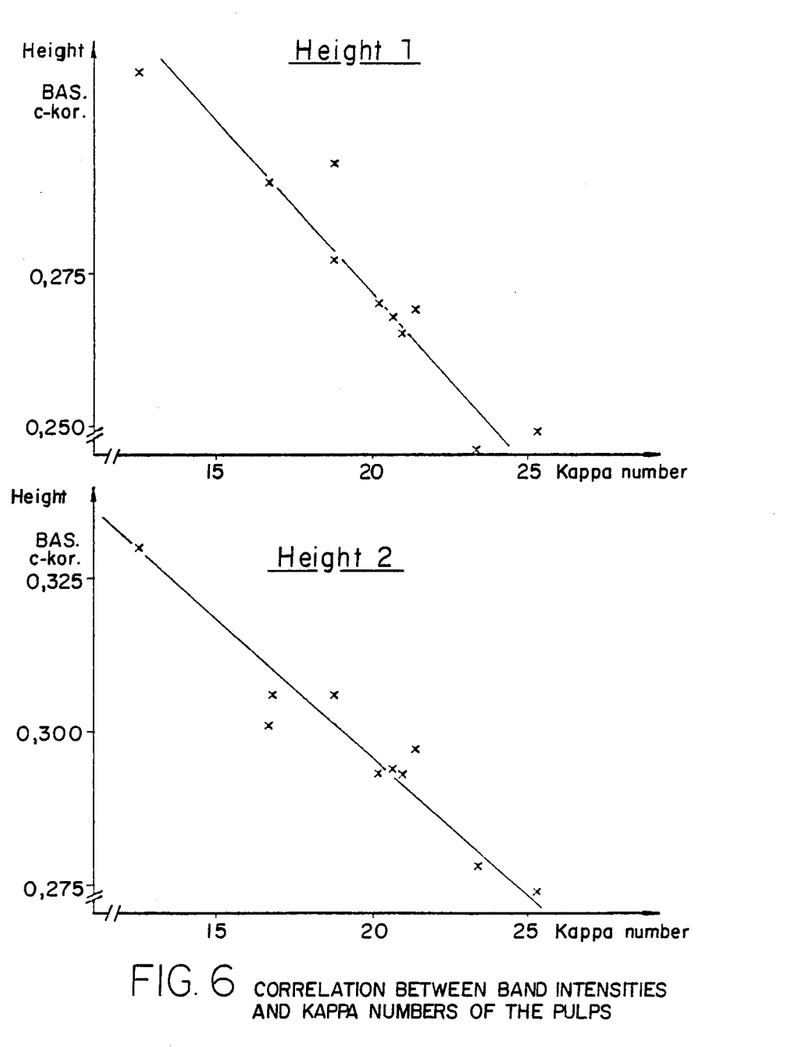

In the same manner described in Example 1 tests were performed for 10 industrial magnesium bisulfite cooks of beech chips. Subsequently the last samples before degassing the digester were evaluated with respect to base-line corrected and liquor/wood corrected band heights and band integrals. Those data were correlated to the kappa numbers of the resulting paper grade pulps by linear regression analysis. Results can be seen in FIG. 5 and 6. The correlation coefficients R had values between 0.79 and 0.95.
Range of cooking conditions:
Cooking liquor concentration:
  5.5–5.8% total $SO_2$
  0.8–1.1% free $SO_2$
  1.35–1.45% MgO
Amount of chips: 64–75 t o.d. weight
Digester: 225 m$^3$ stainless steel
Liquor/wood ratio: 2.1:1–2.8:1
$T_{max}$: 137°–143° C.
Time at $T_{max}$: 240–330 min
p at $T_{max}$: 5.0–5.8 bar
Kappa number of the resulting pulp: 12–26

EXAMPLE 5

Figure 7:
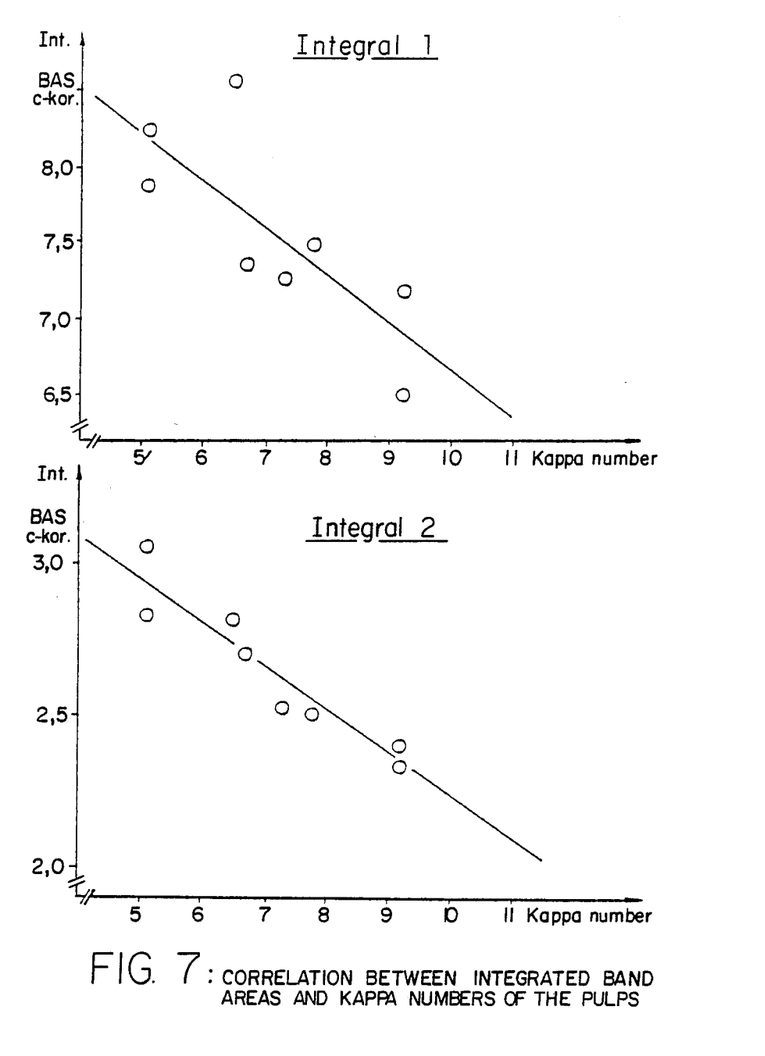
FIGS. 7 and 8 are similar to FIGS. 5 and 6, but using beech chips as described in Example 5.
Figure 8:
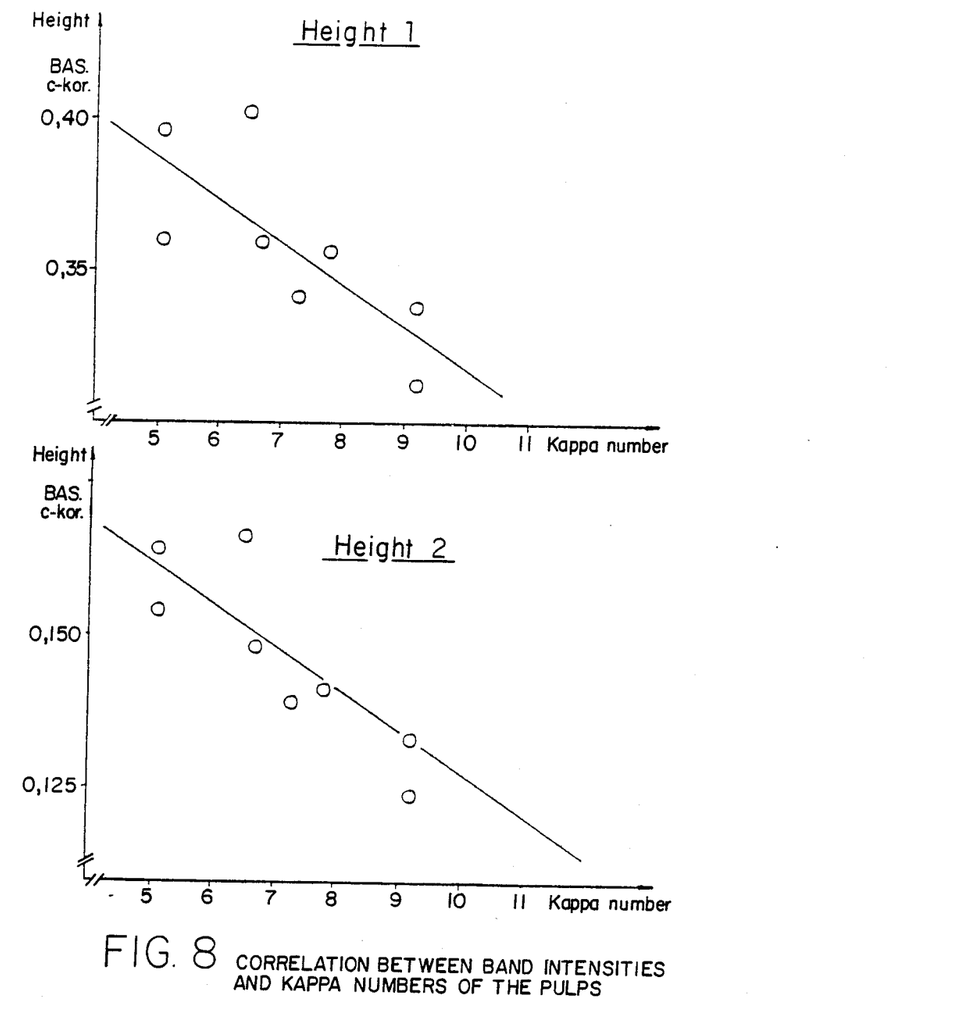

In the same manner described in Examples 1 and 4 tests were performed for 8 industrial magnesium bisulfite cooks of spruce chips for the production of dissolving grade pulps. Plots of the results give FIGS. 7 and 8. The correlation coefficients R had values between 0.75 and 0.94.
Range of cooking conditions:
Cooking liquor concentration:
  7.5–8.5% total $SO_2$
  5.0–6.6% free $SO_2$
  0.75–0.95% MgO
Amount of chips: 55–66 t o.d. weight
Digester: 320 m$^3$ brick-lined steel
Liquor/wood ratio: 3.3:1–4.1:1
$T_{max}$: 136°–142° C.
Time at $T_{max}$: 160–270 min
p at $T_{max}$: 6.5–7.0 bar
Kappa number of the resulting pulp : 5–10

The terms and expressions which have been employed here are used as terms of description and not of limitation, and there is no intention, in the use of such terms and expressions, of excluding equivalents of the features shown and described, or portions thereof, it being recognized that various modifications are possible within the scope of the invention claimed. Furthermore the literature cited above are incorporated herein for additional disclosure.

What is claimed is:

1. A process for controlling the digestion of pulp which comprises:
   (a) subjecting samples of the cooking liquor in the digestion being controlled as the cooking operation proceeds to infra-red spectroscopy at wavenumbers ranging from about 1400 to about 1550 cm$^{-1}$ to produce absorbance curves of the spectra;
   (b) determining base-line corrected band heights or integrals of the absorbance curves of the spectra to the extent needed to establish an IR-data set for each sample;
   (c) obtaining the relationship between the IR spectra of samples of cooking liquor obtained from previous digestions and analytically determined kappa numbers of pulps contained in said previously obtained samples;
   (d) correlating said IR-data sets with said previously obtained relationship to determine the kappa number of the pulp in the said samples of the cooking liquor being digested; and
   (e) using said correlation for optimizing the digestion process by stopping the delignification process when the IR data in said IR-data sets establishes, via the said correlation, that the desired kappa number has been obtained.

2. The process of claim 1 wherein the pulp digestion is performed in the pH-value range of 1-14.

3. The process of claim 1 wherein the pulp digestion is performed as a sulfite process.

4. The process of claim 1 wherein the pulp digestion is performed as a sulfate process.

5. The process of claim 1 wherein the spectroscopy is Fourier transform spectroscopy.

6. The process of claim 1 wherein the spectroscopy is performed in transmission.

7. The process of claim 1 wherein the spectroscopy is performed in attenuated total reflectance.

8. The process of claim 7 in which a circular-ATR-cell is used.

9. The process of claim 1 wherein the spectroscopy is performed in a flow-through cuvette for continuous measurement.

10. The process of claim 1 in which said relationship is obtained using least square curve fitting.

* * * * *